(12) United States Patent
Dannan

(10) Patent No.: US 7,559,887 B2
(45) Date of Patent: Jul. 14, 2009

(54) TOOL INSERTION DEVICE FOR USE IN MINIMALLY INVASIVE SURGERY

(76) Inventor: Patrick Dannan, 746 Fieldston Ter., Webster Groves, MO (US) 63119

( * ) Notice: Subject to any disclaimer, the term of this patent is extended or adjusted under 35 U.S.C. 154(b) by 420 days.

(21) Appl. No.: 11/006,862

(22) Filed: Dec. 8, 2004

(65) Prior Publication Data

US 2006/0122580 A1 Jun. 8, 2006

(51) Int. Cl.
*A61B 1/04* (2006.01)
*A61B 1/00* (2006.01)

(52) U.S. Cl. ...................... 600/114; 600/104

(58) Field of Classification Search .......... 600/101, 600/103, 104, 106, 109, 112, 113, 114, 117, 600/125, 136, 153, 185–199, 221, 227, 228, 600/231, 234; 604/43, 57, 94.01, 164.04, 604/164.11; 606/1
See application file for complete search history.

(56) References Cited

U.S. PATENT DOCUMENTS

| | | | |
|---|---|---|---|
| 3,261,350 A * | 7/1966 | Wallace | 600/182 |
| 3,948,274 A | 4/1976 | Zeldman et al. | |
| 4,799,485 A * | 1/1989 | Furey et al. | 600/193 |
| 5,092,314 A * | 3/1992 | Zeitels | 600/194 |
| 5,207,679 A * | 5/1993 | Li | 606/72 |
| 5,400,768 A * | 3/1995 | McNamara et al. | 600/104 |
| 5,437,644 A * | 8/1995 | Nobles | 604/164.11 |
| 5,441,059 A | 8/1995 | Dannan | |
| 5,716,327 A | 2/1998 | Warner et al. | |
| 5,769,820 A * | 6/1998 | Rammler | 604/104 |
| 6,071,233 A | 6/2000 | Ishikawa et al. | |
| 6,099,468 A * | 8/2000 | Santilli et al. | 600/232 |
| 6,322,538 B1 * | 11/2001 | Elbert et al. | 604/174 |
| 6,767,321 B2 * | 7/2004 | Czarnek et al. | 600/111 |
| 2002/0188175 A1 * | 12/2002 | Levine et al. | 600/159 |
| 2004/0064015 A1 * | 4/2004 | Goto et al. | 600/104 |
| 2005/0192546 A1 * | 9/2005 | Griego et al. | 604/264 |
| 2005/0228224 A1 * | 10/2005 | Okada et al. | 600/104 |

OTHER PUBLICATIONS

International Search Report from corresponding International Application No. PCT/US05/44308, mailed Oct. 31, 2007.
Witten Opinion of the International Search Authority from corresponding International Application No. PCT/US05/44308, mailed Oct. 31, 2007.

* cited by examiner

*Primary Examiner*—Linda C Dvorak
*Assistant Examiner*—Alireza Nia
(74) *Attorney, Agent, or Firm*—Polster, Lieder, Woodruff & Lucchesi, L.C.

(57) ABSTRACT

An insertion tool is provided for use in minimally invasive procedures for inserting surgical instruments, and in particular, camera assemblies, into patient cavities. Also provided is an anchor to position a camera in place in the cavity against an inner surface of the patient tissue.

22 Claims, 8 Drawing Sheets

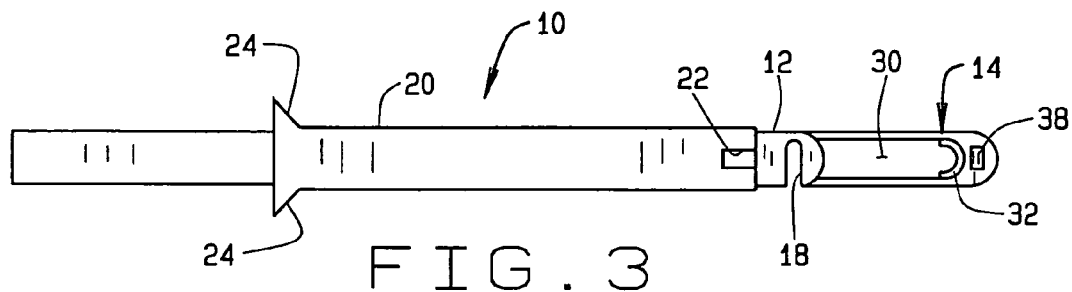
FIG. 3
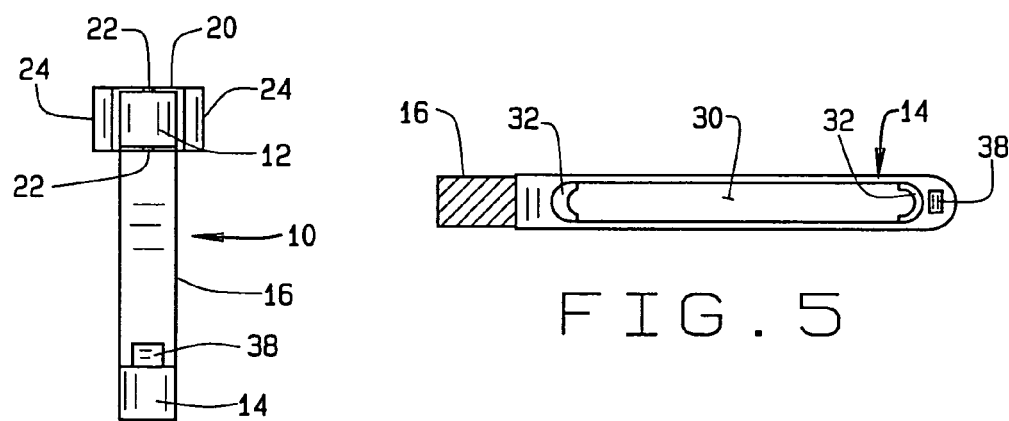
FIG. 4
FIG. 5
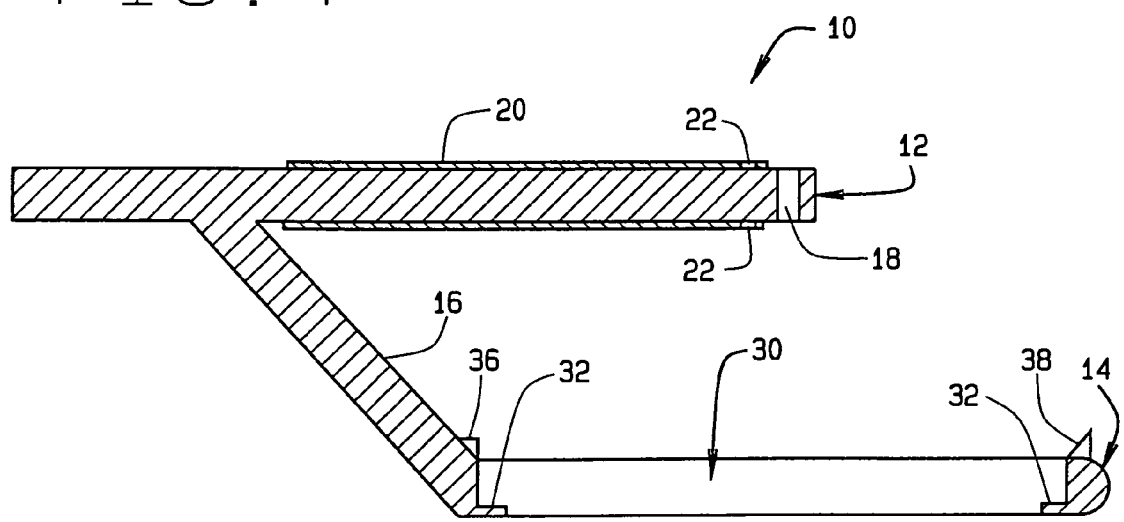
FIG. 6

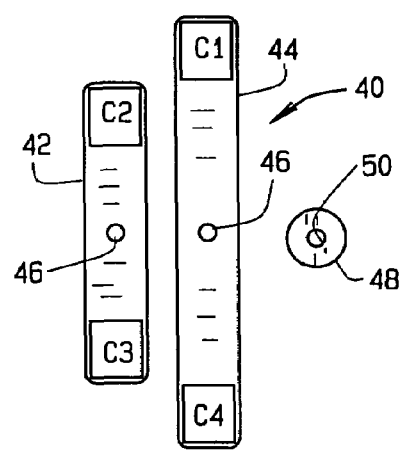
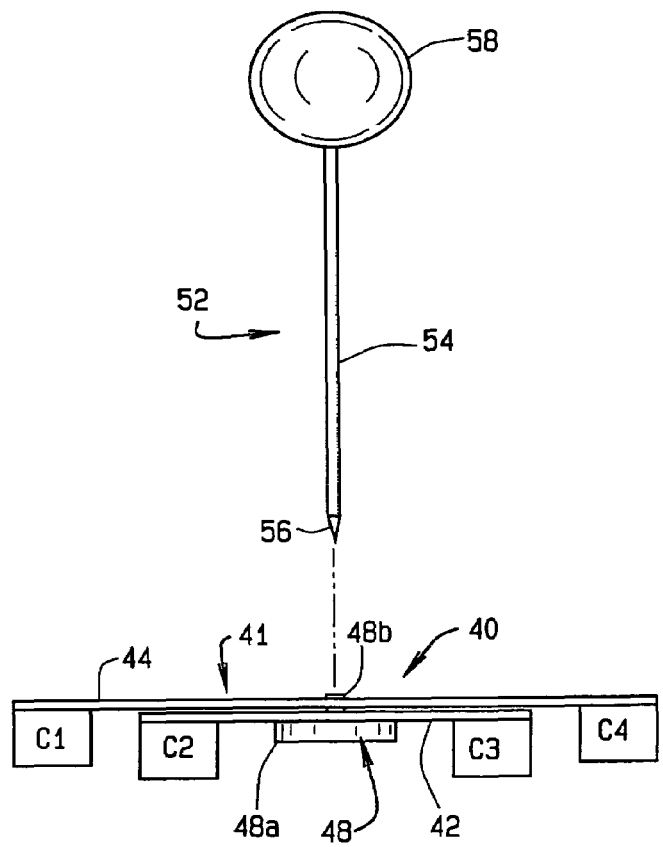
FIG. 7
FIG. 8
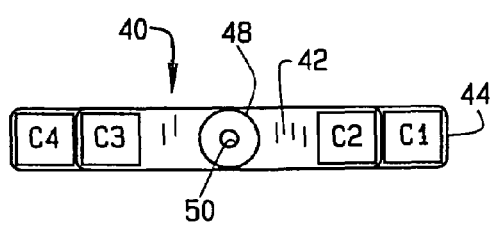
FIG. 9A
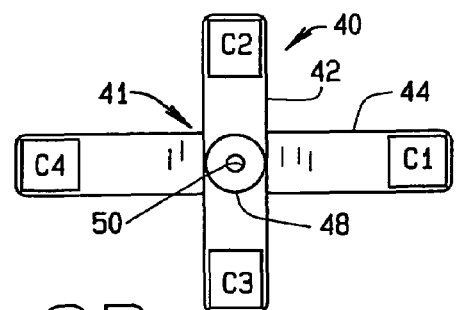
FIG. 9B

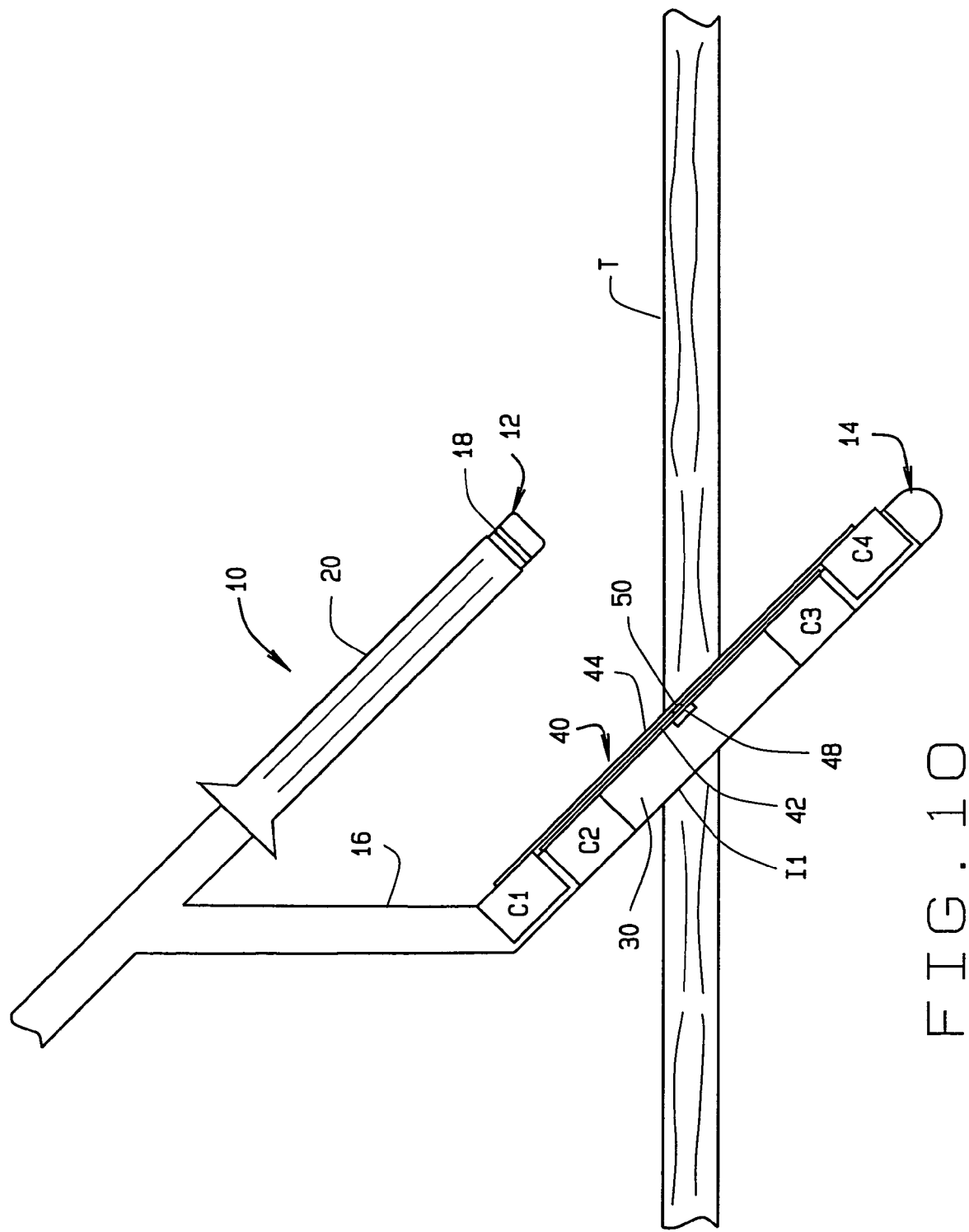

TOOL INSERTION DEVICE FOR USE IN MINIMALLY INVASIVE SURGERY

STATEMENT REGARDING FEDERALLY SPONSORED RESEARCH OR DEVELOPMENT

Not Applicable.

CROSS-REFERENCE TO RELATED APPLICATIONS

Not Applicable.

BACKGROUND OF THE INVENTION

This application relates to devices for use in minimally invasive or endoscopic surgery, and, in particular, to a device which can be used to insert surgical tools into patient cavities, such as an abdominal cavity.

Endoscopic or minimally invasive surgery has become fairly common and is becoming more and more common as surgeons learn and advance endoscopic technology and techniques. Currently, endoscopic surgery is used for procedures conducted in the sinus cavities, on the spine, on knees, on feet, in the abdominal cavity, and in the thoracic cavity. As the technology (i.e., the surgical instruments) and techniques advance, endoscopic surgery will become even more prevalent.

Generally, minimally invasive surgery, when performed in the abdominal cavity, involves making an incision 11 (FIG. 1) in a patient's umbilicus to pass an endoscope E (FIG. 1) into the abdominal cavity A. The endoscope used has a rigid tube T which contains a light source and a camera. Signals from the camera are sent to a monitor to enable a surgeon to view the operating field. A surgical instrument ST is inserted through a second incision 12 in the patient's abdomen. If multiple surgical instruments are needed, then an incision will have to be made for each instrument used.

Because endoscopic surgery involves the use of smaller incisions, and because it generally takes less time than the corresponding conventional abdominal procedure, improvements can still be made. For example, in an abdominal procedure, the abdominal cavity must be inflated to provide space for the surgeon to conduct the procedure. However, some procedures must be conducted without the use of gas. In such gasless procedures, the use of a tissue lifter is required, necessitating making an additional incision, for example, in the patient's abdomen. Further, with the endoscopic tube passing through the patient's navel, the tube T is taking a position that could otherwise be used by other surgical instruments. It would be beneficial to free up the patient's umbilicus for the insertion of additional surgical tools, when and if necessary.

Additionally, with reference to FIG. 1, the tube T extends below the abdominal wall (for abdominal procedures). Hence, the end of the tube T is not fixed in place relative to the abdominal wall. Any movement of the tube T or of the abdominal wall can cause the end of the tube T within the abdominal cavity to move or pivot. As can be appreciated, such moving or pivoting of the end of the tube will change the field of view of the camera. Such changes in the field of view, when unexpected, can make the surgery more difficult. Hence it would also be desirable to provide a camera or imaging system, which is substantially fixed relative to the wall of the cavity in which the camera is positioned.

BRIEF SUMMARY OF THE INVENTION

Briefly stated, an insertion tool is provided to insert a surgical instrument, such as a camera assembly, into a patient cavity, for use in an endodontic or minimally invasive surgical procedure. A surgical instrument used with the insertion tool includes a base having a connection point thereon. An illustrative tool of the invention comprises an extracorporeal arm, an intracorporeal arm, and a segment connecting the intracorporeal arm to the extracorporeal arm. The intracorporeal arm is spaced vertically below the extracorporeal arm. The two arms are generally in the same vertical plane, with the extracoporeal arm extending over at least a portion of the intracorporeal arm. The extracorporeal arm includes an alignment slot therealong. The intracorporeal arm is adapted to removably receive and hold the instrument such that the instrument connection point is vertically aligned with the alignment slot of the extracorporeal arm. To receive the instrument, the intracorporeal arm includes a tray in an upper surface thereof having a shape corresponding generally to the shape of the surgical tool to be placed in the intracorporeal arm. The tray has a depth such that an upper surface of the instrument base does not extend substantially above an upper surface of the intracorporeal arm.

The intracorporeal arm and at least a portion of the segment connecting the intracorporeal arm and extracorporeal arm are sized to pass through an incision of less then about 5 cm, so that the intracorporeal arm can be positioned within the patient cavity. Thus, the intracorporeal arm has a height between its upper and lower surfaces of about 10 mm.

In one embodiment of the invention, the surgical instrument is a camera, and it is desirable to anchor the camera in the cavity. Hence, the insertion tool further includes an anchor having a shaft. The anchor shaft is sized to be removably received in the alignment slot and is adapted at one end thereof to be removably connected to the instrument base connection point. A framework can also be provided to which the anchor is connectable externally of the patient. The framework is sized to extend over a patient positioned on an operating table, and the anchor is adapted to be connected to the framework.

In one embodiment of the insertion tool, the insertion tool can be provided with at least one camera thereon to enable a surgeon to view at least a portion of an upper surface of the intracorporeal arm. A second camera can also be provided. Such cameras, if provided, are positioned or located on either the segment or the upper surface of the intracorporeal arm. The cameras facilitate visualization of the connection of the anchor to the surgical instrument.

A method for using the insertion tool is also disclosed.

BRIEF DESCRIPTION OF THE SEVERAL VIEWS OF THE DRAWINGS

FIG. 3 is a top plan view of the insertion tool;

FIG. 4 is a front elevational view of the insertion tool;

FIG. 5 is a top plan view of an intracorporeal or bottom arm of the insertion tool;

FIG. 6 is a vertical cross-sectional view of the insertion tool;

FIG. 7 is an exploded view of a camera assembly which can be carried by the insertion tool;

FIG. 8 is an exploded view of the camera assembly with an anchoring needle;

FIGS. 9A and 9B show the camera assembly in collapsed and expanded conditions, respectively;

FIG. 10 is a schematic drawing showing the intracorporeal arm of the insertion tool carrying a camera assembly and being passed through an incision in a patient's tissue;

Corresponding reference numerals will be used throughout the several figures of the drawings.

DETAILED DESCRIPTION OF THE INVENTION

Figure 1:
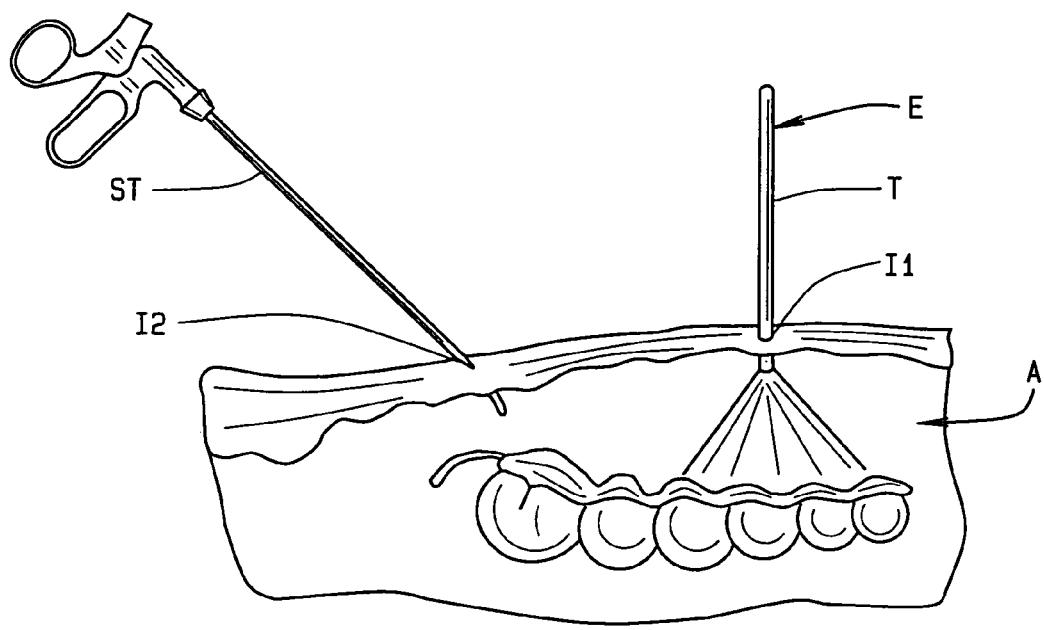
FIG. 1 is a schematic view of a prior art endoscopic procedure.

The following detailed description illustrates the invention by way of example and not by way of limitation. This description will clearly enable one skilled in the art to make and use the invention, and describes several embodiments, adaptations, variations, alternatives and uses of the invention, including what I presently believe is the best mode of carrying out the invention. Additionally, it is to be understood that the invention is not limited in its application to the details of construction and the arrangements of components set forth in the following description or illustrated in the drawings. The invention is capable of other embodiments and of being practiced or being carried out in various ways. Also, it is to be understood that the phraseology and terminology used herein is for the purpose of description and should not be regarded as limiting.

Referring initially to FIGS. 2-6, an insertion tool 10 of the present invention comprises an extracorporeal or upper arm 12 and an intracorporeal or lower arm 14. A segment 16 extends from a back end of the intracorporeal arm 14 to the extracorporeal arm 12 to connect the intracorporeal arm to the extracorporeal arm. Preferably, the segment 16 intersects the extracorporeal arm between the ends thereof to form a forward section 12a and a rearward section 12b. The rearward section 12b forms a handle section which can be grasped by a surgeon or other practitioner to use and position the insertion tool 10, as will be described below.

Figure 2:
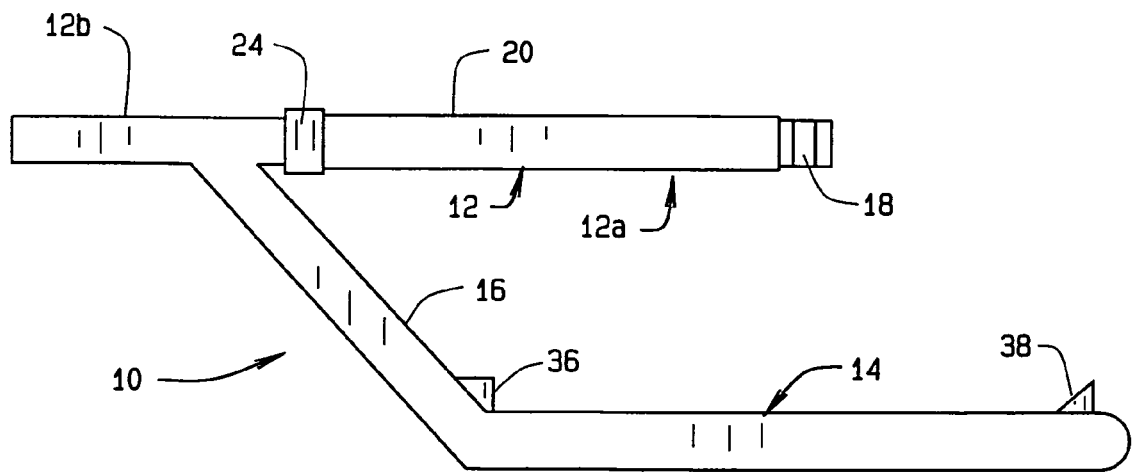
FIG. 2 is a side elevational view of one illustrative embodiment of an insertion tool of the present invention used to position a surgical instrument, such as a camera assembly, beneath a patient's tissue.

The extracorporeal arm 12 includes a slot 18 shown to be near the forward end of the extracorporeal arm 12. The slot 18 extends inwardly from a side of the arm and extends through the extracorporeal arm, from the top surface to the bottom surface, as seen in FIGS. 2 and 6. The slot 18 is shown to extend generally perpendicularly to the side of the extracorporeal arm 12, but could extend at other angles if desired.

A slide tube 20 is received on the extracorporeal arm forward portion 12a to be axially slidable along the extracorporeal arm. The slide tube 20 is provided with opposed slots 22 which extend rearwardly from the forward end of the tube. The tube slots 22 are positioned, such that, when the slide tube 20 is moved forwardly, as seen for example in FIG. 10, the tube slots 22 will intersect the extracorporeal arm slot 18 to form aligned openings in the upper and lower surfaces of the tool extracorporeal arm 12. The slide tube 20 movable relative to said extracorporeal arm 12 between a first position in which said alignment slot 18 is open at the edge of the extracorporeal arm and a second position in which said alignment slot is closed at the edge of the extracorporeal arm. In this second position, the slide tube 20 and the slot 18 in combination define a hole through the extracorporeal arm 12 which is closed around the perimeter of the hole. To facilitate axial movement of the tube 20 along the extracorporeal arm 12, the tube 20 is provided with finger pulls 24, shown in the drawings to be positioned at the back of the tube 20. The tube 20 is rotationally keyed relative to the extracorporeal arm 12 to prevent rotation of the tube 20 relative to the extracorporeal arm 12. To this end, the tube 20 and extracorporeal arm 12 are both shown to be square in cross-section. Other shapes could be used as well which would prevent rotation of the tube 20 relative to the extracorporeal arm 12. For example, a groove could be provided in the one of the extracorporeal arm 12 and tube 20 and a rib or projection could be provided in the other of the extracorporeal arm and tube 20 which would ride in the groove to prevent rotation.

The lower or intracorporeal arm 14 includes a tray 30 in its upper surface. The tray 30 is shown to be in the form of an elongate slot which extends vertically through the intracoropreal arm 14. However, the tray could, if desired, extend only partially through the intracoropreal arm 14. The tray 30 is positioned along the intracoropreal arm 14 such that it is vertically beneath the upper or extracorporeal arm 14, and in particular, beneath the extracorporeal arm slot 18, as seen in FIGS. 2 and 6. The tray 30 is sized to receive a surgical instrument which will be utilized during an endoscopic procedure. One such instrument is a camera assembly 40 shown in FIGS. 7 and 8. To this end, the tray 30 is provided with seats 32 upon which the camera assembly rests. The tray 30 has a depth, such that when the surgical instrument is placed in the tray, the top of the surgical instrument will not extend substantially above the upper surface of the intracoropreal arm 14, and preferably, such that the top of the surgical instrument is generally flush with the upper surface of the intracoropreal arm 14. The tray 30 is also shaped such that the instrument will be retained in the tray during insertion of the intracorporeal arm 14 through an incision, but will also allow for easy disengagement of the intracorporeal arm 14 from the tray 30, as will be described below.

The insertion tool 10 can be provided with cameras 36 and 38 which are shown positioned at opposite ends of the intracorporeal arm 14. The camera 36 is positioned adjacent the connecting segment 16 and faces the free end of the arm 14; and the camera 38 is positioned at the free end of the arm 14 and faces generally rearwardly. If desired, only one of the cameras can be provided, or both cameras can be omitted. The cameras 36 and 38, if provided, are in communication with a monitor in the operating room so that the images of from the cameras can be seen.

A camera assembly 40 which can be placed in the insertion tool tray 30 to be inserted into a body is shown in FIGS. 7 and 8. The camera assembly 40 includes a base or platform 41 formed form a pair of arms 42 and 44. Cameras C2 and C3 are shown fixed to the opposite ends of arm 42; and cameras C1 and C4 are shown fixed to the opposite ends of arm 44. The cameras C1-C4 can be any desired type of camera. For example, they could be CCD or CMOS cameras which can be fitted on a chip which is placed on the platform arms 42 and 44. Alternatively, the cameras could comprised fiber optics which end at the blades and are connected to an external light source and camera.

Arm 42 is shorter than arm 44, such that the arms, with the cameras, can be stacked, as seen in FIG. 8. The arms 42 and 44 are each provided with a central opening 46, and a connector 48 is provided to connect the two arms together to form the platform 41. The connector 48 is shown to include a base 48a having a neck 48b sized to extend through both the platform openings 46. The neck 48b is sized and shaped to connect the two platforms together, and to allow for the platforms to be rotated relative to each other from a collapsed or folded position shown in FIG. 9A to an expanded position shown in FIG. 9B. As seen in FIG. 9A, in the collapsed or folded position, the cameras on the shorter arm 42 are positioned between the cameras of the longer arm 44. The connector 48 includes an opening 50. The cameras C1-C4, as will be appreciated, are all operatively in communication with a computer system and/or a monitor to allow for visualization of the surgical site within a patient's body.

An anchor 52 is provided to position the camera assembly 40 within the patient's body during an endoscopic procedure. The anchor 52 includes shaft 54 having a lower end 56 adapted to be passed through a patient's tissue (such as through the patient's abdominal wall). The lower end 56 is sized to be received in the camera assembly connector opening 50, and to mate with, or be joined to, the connector 48. To this end, the connector opening 50 can be provided with an L-shaped slot which opens to the upper surface of the connector neck 48b, and the shaft 54 can be provided with a projection which is received in the slot, such that the shaft and connector cooperate to form a bayonet type connection. In such a bayonet connection, the projection could be on the connector 48 and the L-shaped slot could instead be on the anchor shaft 54. Other types of connections can be used as well. For example, the end of the shaft 54 and the connector opening 50 could be threaded to form a threaded connection between the shaft 56 and the connector 48. As can be appreciated, the connector 48 defines a connection point on the camera assembly for connection of the camera assembly 40 to the anchor shaft 54. At its upper end, the anchor is provided with a member 58 (shown as a ball), which is adapted to connect the anchor to a platform holder or support, as will be described below.

If the cameras C1-C4 comprise fiber optics which are operatively connected to external light sources and cameras, the fiber optics would extend through the anchor shaft 54. Additional fiber optics would extend from the connection point on the platform 41 and extend along the platform arms 42 and 44. The fiber optics on the platform arms would be operatively connected to the fiber optics in the anchor shaft. If the cameras are chip mounted cameras (i.e., CCD or CMOS cameras), then the cameras would be in communication with a computer or monitor either by a wired or wireless connection. In the case of a wired connection, wires would pass along the platform arms and through the anchor shaft. Again, there would be a connection between the arm wires and the wires in the shaft.

Use of the insertion tool 10 is shown schematically in FIGS. 10-13. Initially, the surgical tool (in the illustrated example—the camera assembly 40) is inserted in the tool tray 30. The camera assembly 40 is in the collapsed position (as seen in FIG. 9A), the cameras C1 and C4 rest on the tray seats 32 and the longer platform arm 44 (which is above the shorter platform arm 42) is spaced only slightly above the upper surface of the intracorporeal arm 14. Importantly, the tray is positioned along the intracorporeal arm 14 such that, when the camera assembly is received in the tray 30, the camera assembly connection point is vertically aligned with the slot 18 of the extracorporeal arm 12.

With the surgical instrument received in the tray, the intracorporeal arm 14 is passed through an incision I1 in the patient's tissue T. For example, if the procedure is an appendectomy, the incision I1 is made in the patient's abdominal wall. Depending on what procedure is being performed, the tissue T can be on the patient's back, chest, neck, etc. The segment 16 extending between the intracorporeal arm 14 and the extracorporeal arm 12 is sufficient such that the intracorporeal arm 14 can be spaced from an inner surface SI (FIG. 11) of the tissue T and the extracorporeal arm can be spaced from the outer surface SO of the tissue T.

Figure 11:
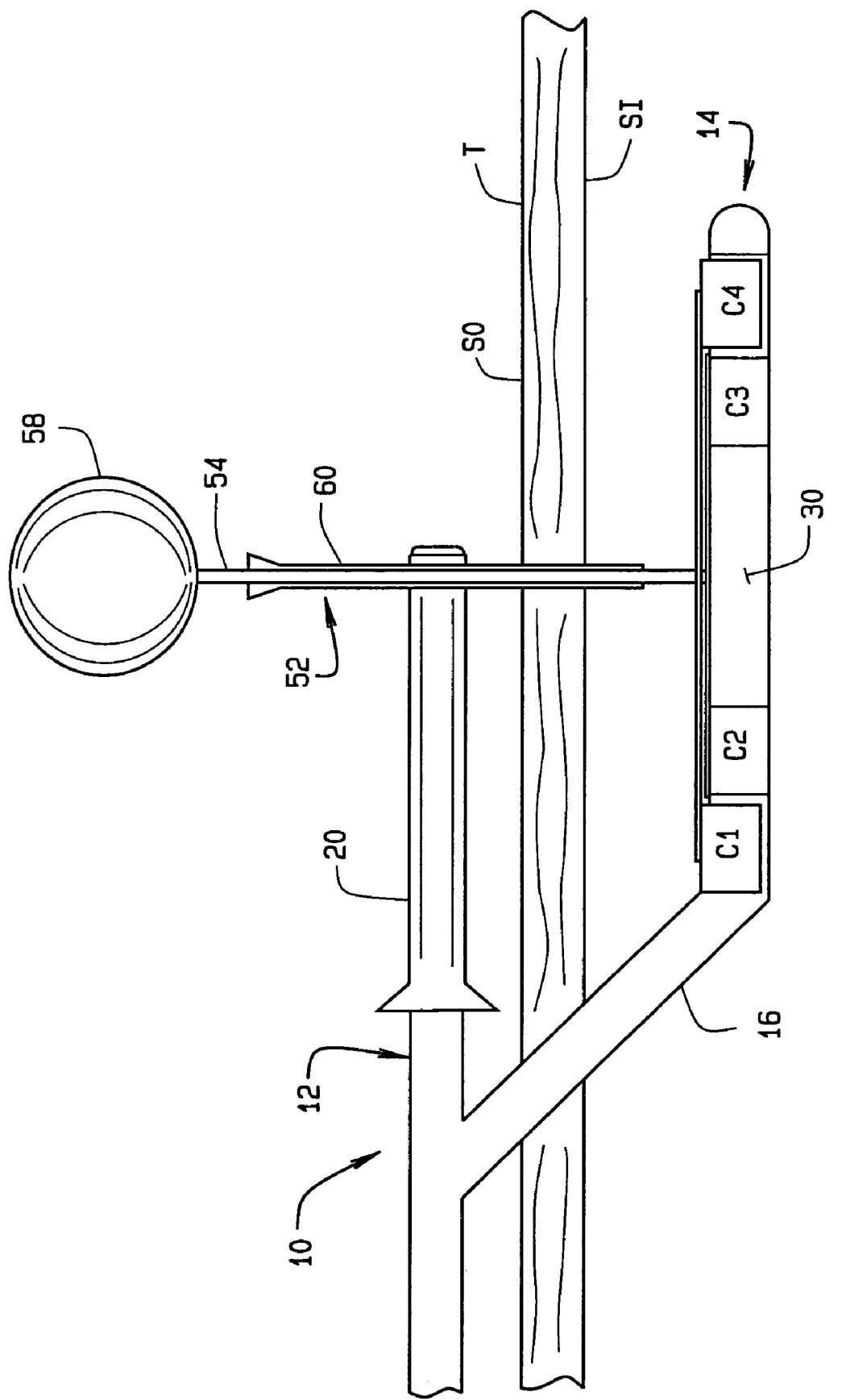
FIG. 11 is a schematic drawing showing an anchoring shaft passed through an extracorporeal or upper arm of the insertion tool, through the patient tool to be connected to the camera assembly.

When the intracorporeal arm 14 is inserted into the patient, as seen in FIG. 11, the slide tube 20 (if not already in a forward position) is moved forwardly along the extracorporeal arm 12 such that the slide tube slots 22 intersect the arm slot 18 to form an enclosed opening which is aligned with the connection point of the camera assembly 40.

A hollow sheath 60 is passed through the opening formed by the intersecting or crossing slots 18 and 22; and the anchor shaft 56 is passed through the sheath 60. The sheath 60 can be a trocar which is used to form an opening in the tissue T through which the anchor shaft 56 can pass. Alternatively, the shaft 56 can be used to puncture the tissue T to allow the shaft 56 and sheath 60 to pass through the tissue. When the shaft 56 is passed through the tissue T, it will be aligned with the connection point (i.e., the opening 50 of the camera assembly connector 48) and the shaft 56 can be advanced until it engages the camera assembly connection point. Once engaged with the camera assembly, the shaft 56 can be connected to the connector 48 as described above. The cameras 36 and 38 will allow for the surgeon to view the progress of the anchor shaft into the patient cavity as the shaft is passed through the tissue T and to monitor the connection of the shaft 54 to the camera assembly 40. The vertical alignment of the extracorporeal arm 12 with the camera assembly connection point, in combination with the top-to-bottom height of the arm 14 will substantially ensure that the anchor shaft 54 will engage the connection point of the camera assembly, and the connection of the anchor to the camera assembly could be accomplished without the aid of the cameras 36 and 38 if desired. The sheath 60 is used to maintain an open port to prevent the tissue T from binding on the anchor shaft 54 during insertion or removal.

Figure 14:
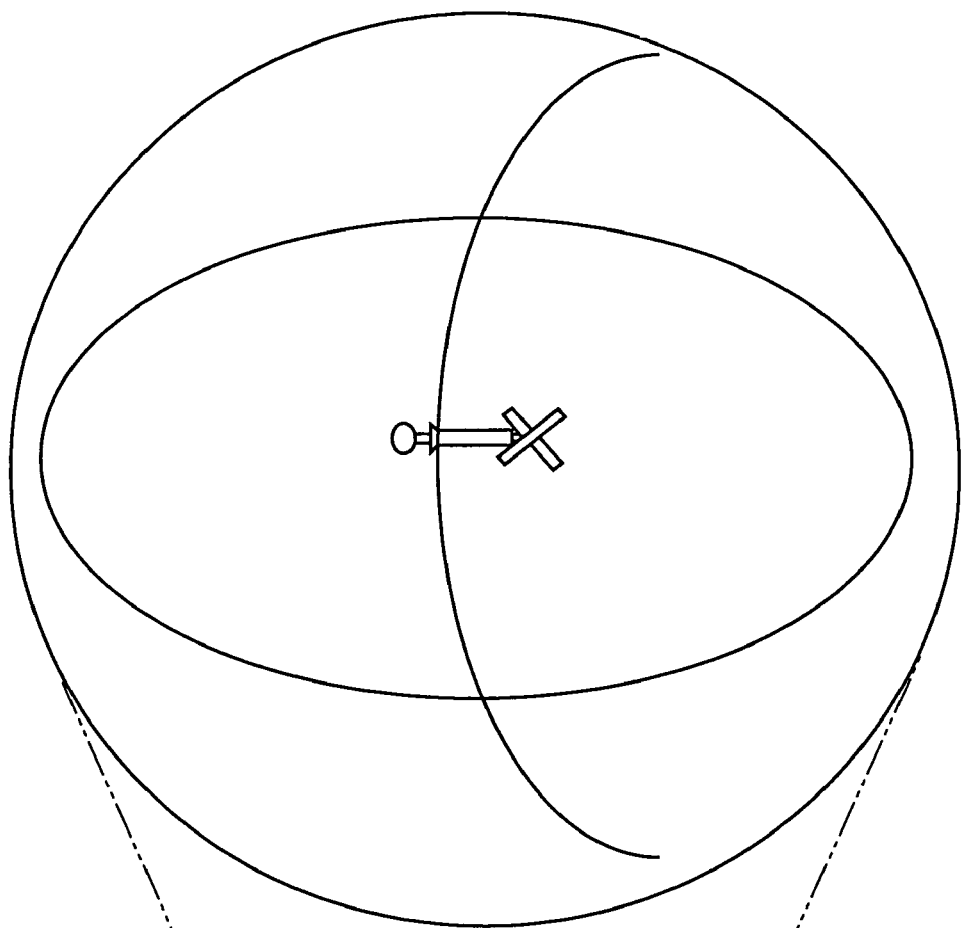
FIG. 14 is a schematic drawing showing the connection of an upper end of the anchoring shaft to a support framework.

With the anchor 52 connected to the camera assembly 40, the top of the anchor can be connected to a holder 62 which is shown schematically in FIG. 14. The holder 62 comprises a frame which is connected to the rails 64 on a surgical table 66. The holder frame 62 extends over the patient P, and the end 58 of the anchor 52 is adapted to be connected to the holder frame 62. As can be appreciated, when the anchor 52 is connected to the holder 62, the holder 62 will hold the camera assembly 40 against the inner surface SI of the tissue T during the procedure.

Figure 12:
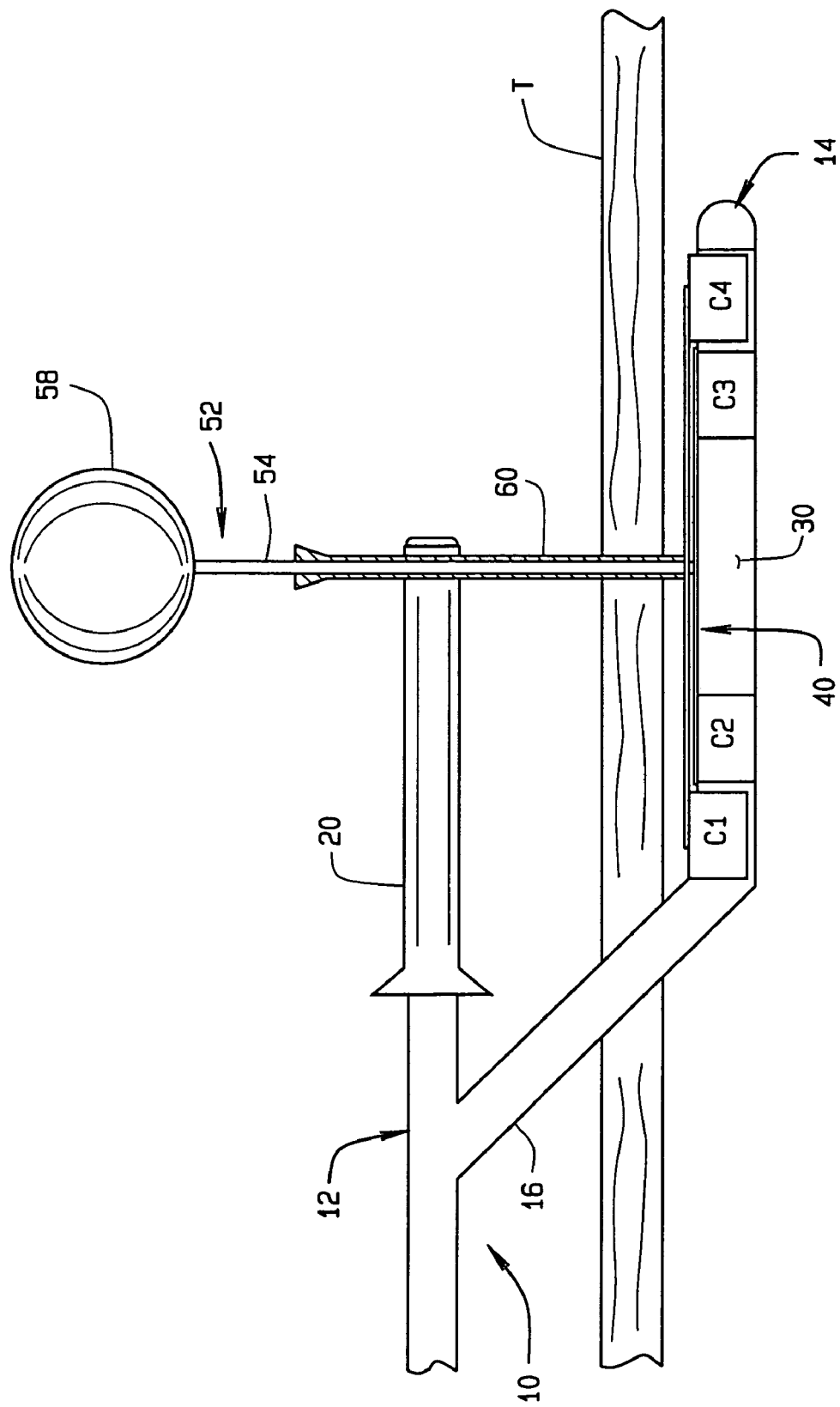
FIG. 12 is a schematic drawing showing the insertion tool in a position in preparation for separation from the surgical instrument.
Figure 13:
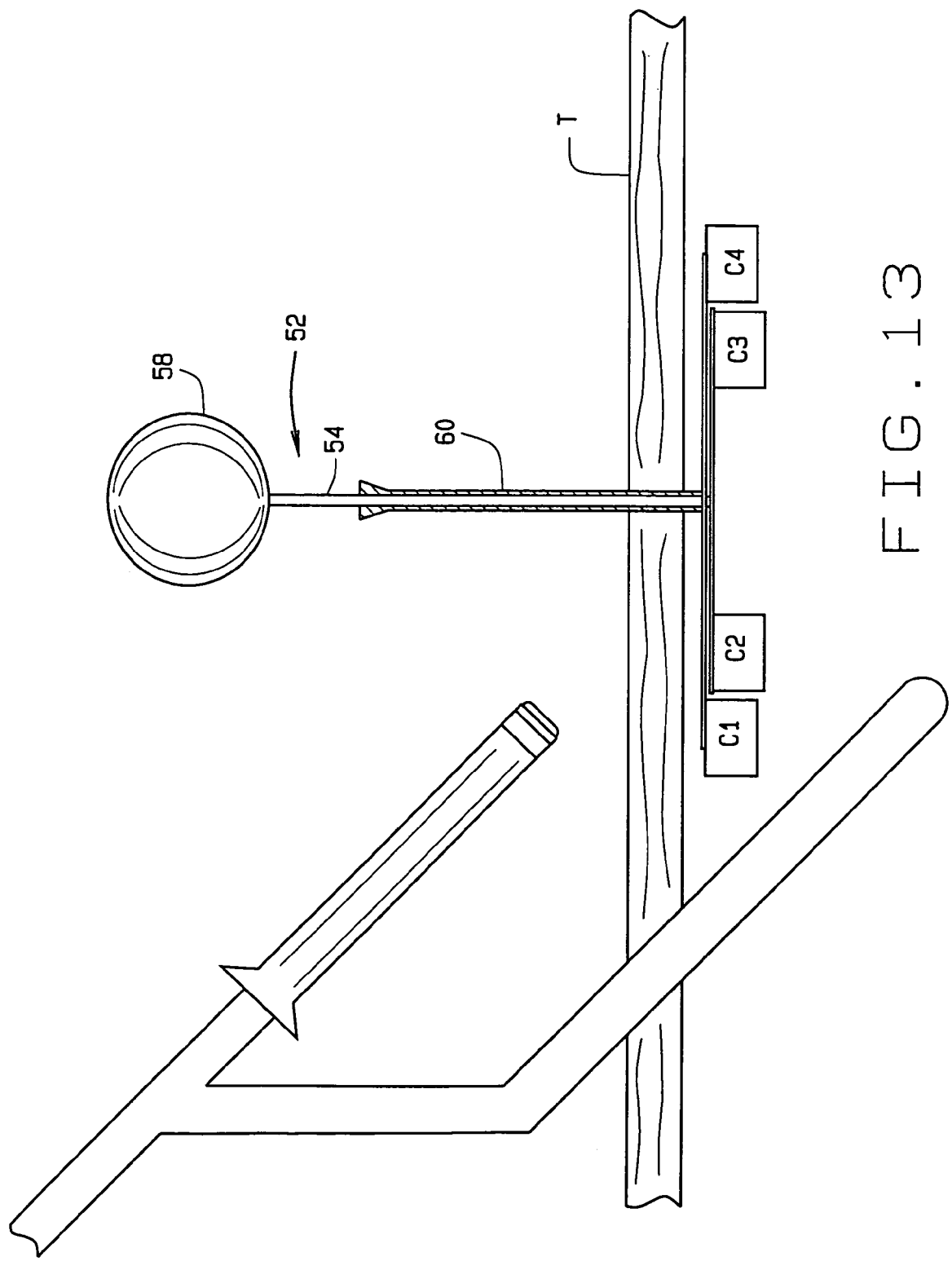
FIG. 13 is a schematic drawing showing the withdrawal of the insertion tool from the surgical instrument and from the patient.

When the anchor 52 is connected to the holder 62, the insertion tool can be disconnected from the anchor and camera assembly, and removed from the patient body, as seen in FIGS. 12 and 13. With the camera assembly anchored in place, the insertion tool can be lowered relative to the anchor shaft (and hence relative to the camera assembly 40) to disengage the camera assembly from the insertion tool tray 30. Once the intracorporeal arm is clear of the camera assembly 40, the slide tube 20 can be moved rearwardly relative to the extracorporeal arm to open the extracorporeal arm slot 18. When the slot 18 is opened, as seen in FIG. 12, the insertion tool can be pivoted relative to the anchor shaft 54 and the sheath 60, such that the insertion tool is fully disengaged from both the camera assembly and the anchor 52. The insertion tool can then be removed from the patient.

When the procedure is completed, the insertion tool can be inserted back into the cavity through the incision 11. The camera assembly can be closed and then received in the insertion tool tray 30. The anchor 52 can be disconnected from the camera assembly 40, and then the insertion tool can be used to remove the camera assembly from the patient.

As can be appreciated, with the insertion tool removed from patient during the procedure, the port used to insert the camera assembly into the patient cavity will then be free to receive a surgical instrument for use by the surgeon. This will reduce the number of incisions which would otherwise be required to conduct the endoscopic or minimally invasive surgery. Further, the camera assembly will be supported or held against the inner surface of the tissue, substantially preventing the camera from pivoting relative to the cavity, as could occur with the prior art system (shown in FIG. 1). Additionally, because the camera assembly is held against the inner surface of the cavity, the camera platform itself can be used as a lifter, eliminating the need for a separate lifter, if the procedure being conducted requires the use of a lifter.

As various changes could be made in the above constructions without departing from the scope of the invention, it is intended that all matter contained in the above description or shown in the accompanying drawings shall be interpreted as illustrative and not in a limiting sense.

The invention claimed is:

1. In combination, a surgical instrument for use during endoscopic treatment and an insertion tool for inserting the instrument into a patient cavity;
   a. the instrument comprising a base having a connection point thereon;
   b. the insertion tool comprising an extracorporeal arm, an intracorporeal arm, and a segment connecting said intracorporeal arm to said extracorporeal arm; said intracorporeal arm being spaced below said extracorporeal arm; said intracorporeal arm and said extracorporeal arm being generally in the same vertical plane; said extracorporeal arm extending over at least a portion of said intracorporeal arm; said extracorporeal arm comprising an alignment slot therealong; said alignment slot opening to an edge of said extracorporeal arm; said tool further comprising a slide tube movable relative to said extracorporeal arm between a first position in which said alignment slot is open at said edge of said extracorporeal arm and a second position in which said alignment slot is closed at said edge of said extracorporeal arm, and in which said slide tube and said slot in combination define a hole through said extracorporeal arm which is closed around the perimeter of said hole; said intracorporeal arm having an upper surface, a lower surface, and an upwardly opening tray in said upper surface, said tray having side walls, a front wall and a back wall and being aligned with said slot of said extracorporeal arm and being adapted to removably receive and hold said instrument such that said instrument connection point is aligned with said alignment slot of said extracorporeal arm when said instrument is received in and held by said tray.

2. The combination of claim 1 wherein said intracorporeal arm and at least a portion of said segment are sized to pass through an incision of less then about 5 cm.

3. The combination of claim 1 wherein said intracorporeal arm has a height between its upper and lower surfaces of about 10 mm.

4. The combination of claim 1 wherein said tray in said insertion tool intracorporeal arm has a shape corresponding to the shape of said instrument.

5. The combination of claim 4 wherein said tray has a depth such that an upper surface of said instrument base does not extend substantially above an upper surface of said intracorporeal arm.

6. The combination of claim 1 further comprising an anchor having a shaft; said anchor shaft being sized to be removably received in said alignment slot and adapted at one end thereof to be removably connected to said instrument base connection point.

7. The combination of claim 6 further comprising a framework having a portion sized to extend over a patient positioned on an operating table; said anchor being adapted to be connected to said framework.

8. The combination of claim 1 wherein said insertion tool further includes at least one camera; said camera being positioned on said insertion tool to enable a surgeon to view at least a portion of said upper surface of said intracorporeal arm.

9. The combination of claim 8 wherein said at least one camera is located on one of said segment and said intracorporeal arm upper surface.

10. The combination of claim 9 including at least a second camera located on the other of said segment and said intracorporeal arm upper surface.

11. An insertion device for inserting a surgical tool into a patient cavity for use in an endoscopic procedure; the surgical tool comprising an instrument base connection point; the insertion device comprising an extracorporeal arm, an intracorporeal arm, and a segment connecting said intracorporeal arm to said extracorporeal arm; said intracorporeal arm being spaced below said extracorporeal arm; said intracorporeal arm and said extracorporeal arm being generally in the same vertical plane; said extracorporeal arm extending over at least a portion of said intracorporeal arm; said extracorporeal arm comprising an alignment slot therealong; said intracorporeal arm having an upper surface, a lower surface, and an upwardly opening tray in said upper surface; said tray having side walls, a front wall and a back wall to define cavity; said tray being shaped to retain the surgical tool in the tray during insertion of the intracorporeal arm through an incision in a patient; said tray being aligned with said slot of said extracorporeal arm and being adapted to removably receive and hold said surgical tool such that said instrument connection point is aligned with said alignment slot of said extracorporeal arm when said surgical tool is received in and held by said tray.

12. The insertion device of claim 11 wherein said segment has a first end connected to said intracorporeal arm at an end of said intracorporeal arm and a second end connected to said extracorporeal arm at a point between opposite ends of said extracorporeal arm.

13. The insertion device of claim 11 wherein said intracorporeal arm and at least a portion of said segment are sized to pass through an incision of less then about 5 cm.

14. The insertion device of claim 11 wherein said intracorporeal arm has a height between its upper and lower surfaces of about 10 mm.

15. The insertion device of claim 11 wherein said tray in said insertion tool intracorporeal arm has a shape corresponding to the shape of the surgical tool.

16. The insertion device of claim 15 wherein said tray has a depth sized relative to the surgical tool to be received therein such that an upper surface of said tool does not extend substantially above an upper surface of said intracorporeal arm.

17. The insertion device of claim 11 further comprising an anchor having a shaft; said anchor shaft being sized to be removably received in said alignment slot and adapted at one end thereof to be removably connected to said instrument base connection point.

18. The insertion device of claim 11 wherein said insertion tool further includes at least one camera; said camera being positioned on said insertion tool to enable a surgeon to view at least a portion of the upper surface of said intracorporeal arm.

19. The insertion device of claim 18 wherein said at least one camera is located on one of said segment and said intracorporeal arm upper surface.

20. The insertion device of claim 19 including at least a second camera located on the other of said segment and said intracorporeal arm upper surface.

21. An insertion device for inserting a surgical tool into a patient cavity for use in an endoscopic procedure; the insertion device comprising:
   a. an extracorporeal arm;
   b. an intracorporeal arm operatively connected to said extracorporeal arm and spaced vertically below said extracorporeal arm to be generally in the same vertical plane as said extracorporeal arm; said extracorporeal arm extending over at least a portion of said intracorporeal arm; said intracorporeal arm comprising an upper surface, a lower surface and upwardly opening tray in said upper surface for receiving the surgical tool from a direction normal to said intracorporeal arm and for removably holding the surgical tool in the intracorporeal arm against movement of the surgical tool relative to the intracorporeal arm; said tray having side walls, a front wall and a back wall to define cavity; said tray being shaped to retain the surgical tool in the tray during insertion of the intracorporeal arm through an incision in a patient;
   c. anchoring means connectable to the surgical tool for anchoring said surgical tool against an inner surface of a patient cavity; said anchoring means having a first end and a second end; said first end being adapted to be removably connected to said surgical tool; and
   d. aligning means in said extracorporeal arm for receiving said anchoring means through an edge of said extracorporeal arm and for aligning said anchoring means first end with a connection point on said surgical tool to facilitate connection of said anchoring means first end to the surgical tool; said aligning means being aligned with said receiving means of said intracorporeal arm;
   e. a slide tube movable relative to said extracorporeal arm between a first position in which said aligning means can receive said anchoring means though said edge of said extracorporeal arm and a second position in which said aligning means is closed to prevent removal of said anchoring means through said edge of said extracorporeal arm.

22. The insertion device of claim 21 wherein said aligning means comprises a slot in said extracorporeal arm; said slot being sized to receive said anchoring means and being positioned vertically above said intracorporeal arm receiving means.

\* \* \* \* \*